United States Patent [19]

Turnlund et al.

[11] Patent Number: 5,766,710

[45] Date of Patent: Jun. 16, 1998

[54] BIODEGRADABLE MESH AND FILM STENT

[75] Inventors: Todd Hanson Turnlund, Mountain View; Robert Paul Eury, Cupertino, both of Calif.

[73] Assignee: Advanced Cardiovascular Systems, Inc., Santa Clara, Calif.

[21] Appl. No.: 666,755

[22] Filed: Jun. 19, 1996

Related U.S. Application Data

[62] Division of Ser. No. 266,964, Jun. 27, 1994, Pat. No. 5,629,077.

[51] Int. Cl.$^6$ ............................................. B29D 22/00
[52] U.S. Cl. ........................ 428/36.1; 156/148; 156/218; 156/308.2; 156/309.6; 428/36.3; 442/38; 623/1; 623/DIG. 900; 604/8
[58] Field of Search ........................ 623/1, DIG. 900; 604/8; 156/218, 308.2, 309.6, 148; 442/38; 428/36.1, 36.3

[56] References Cited

U.S. PATENT DOCUMENTS

| 3,900,632 | 8/1975 | Robinson . |
| 4,110,497 | 8/1978 | Hoel . |
| 4,346,028 | 8/1982 | Griffith . |
| 4,633,873 | 1/1987 | Dumican et al. . |
| 4,718,907 | 1/1988 | Karwoski et al. . |
| 4,740,207 | 4/1988 | Kreamer . |
| 4,768,507 | 9/1988 | Fischell et al. . |
| 4,879,135 | 11/1989 | Greco et al. . |
| 5,059,211 | 10/1991 | Stack et al. . |

(List continued on next page.)

FOREIGN PATENT DOCUMENTS

| 0 108 171 | 5/1984 | European Pat. Off. . |
| 0 144 534 | 6/1985 | European Pat. Off. . |
| 0 397 500 | 11/1990 | European Pat. Off. . |
| 0 464 755 | 1/1992 | European Pat. Off. . |
| 0 554 082 A1 | 8/1993 | European Pat. Off. . |
| 0 621 017 A1 | 10/1994 | European Pat. Off. . |
| 2 247 696 A1 | 3/1992 | United Kingdom . |
| WO 91/17789 | 5/1991 | WIPO . |
| WO 92/10218 | 6/1992 | WIPO . |
| WO 93/06792 | 4/1993 | WIPO . |

OTHER PUBLICATIONS

"Totally Resorbable High-Strength Composite Material," by Benjamin S. Kelley, Richard L. Dunn and Robert A. Casper, *Advances in Biomedical Polymers* Edited by Charles G. Gebelein.

"A View of Vascular Stents" by Richard A. Schatz, M.D. from the Arizona Heart Institute Foundation, Phoenix, Arizona (1988).

"Fiber-Reinforced Absorbable Composite for Orthopedic Surgery" by R.A. Casper, B.S. Kelley, R.L. Dunn, A.G. Potter, and D.N. Ellis in *Polymeric Materials Science and Engineering*, Proceedings of the ACS DivisiofPlyei Mtra: Science and Engineering, vol. 53, Fall Meeting 1985.

*Primary Examiner*—James J. Bell
*Attorney, Agent, or Firm*—Fulwider Patton Lee & Utecht, LLP

[57] ABSTRACT

The biodegradable mesh and film stent for use in blood vessels is formed of a sheet of a composite mesh material formed of biodegradable high strength polymer fibers bonded together with a second biodegradable adhesive polymer, and laminated on at least one side with a thin film of a third biodegradable polymer. The biodegradable mesh and film material is formed as a sheet and cut in a shape that can be used as a stent, such as a "belt-buckle" type shape, the ends of which can be joined in a contractible, expandable loop. In the method of making the biodegradable composite mesh and film stent, the composite mesh is preferably formed from a weave formed of high strength biodegradable polymeric fibers, and a plurality of low temperature melting biodegradable polymeric fibers. In an alternate embodiment, the high strength fibers are commingled with the low temperature melting fibers. In another alternate embodiment, the high strength fibers are coated with the low temperature melting polymer. The composite mesh is covered on at least one side by a laminating film, and is then cut into the shape of the stent.

34 Claims, 3 Drawing Sheets

U.S. PATENT DOCUMENTS

| | | |
|---|---|---|
| 5,062,829 | 11/1991 | Pryor et al. . |
| 5,084,065 | 1/1992 | Weldon et al. . |
| 5,085,629 | 2/1992 | Goldberg et al. . |
| 5,108,755 | 4/1992 | Daniels et al. . |
| 5,163,951 | 11/1992 | Pinchuk et al. . |
| 5,167,614 | 12/1992 | Tessmann et al. . |
| 5,197,977 | 3/1993 | Hoffman, Jr. et al. . |
| 5,236,447 | 8/1993 | Kubo et al. . |
| 5,383,925 | 1/1995 | Schmitt . |
| 5,385,580 | 1/1995 | Schmitt . |

5,766,710

1

BIODEGRADABLE MESH AND FILM STENT

This is a division of application Ser. No. 08/266,964, filed Jun. 27, 1994 now U.S. Pat. No. 5,629,077.

BACKGROUND OF THE INVENTION

1. Field of the Invention

This invention relates generally to expandable intraluminal vascular grafts, generally referred to as stents, and more particularly concerns biodegradable mesh stents reinforced with a biodegradable film laminate capable of releasing therapeutic drugs.

2. Description of Related Art

Stents used to maintain patency of vessels in the body are typically implanted within a vessel in a contracted state, and expanded once in place in the vessel to allow fluid flow through the vessel and the stent. Such a stent can be moved along a guide wire previously placed in the vessel, and expanded by inflation of a balloon within the stent. Deflation of the balloon and removal of the guide wire leaves the stent in place in the vessel, locked in an expanded state. It has been found that continued exposure of the stent to blood can lead to undesirable thrombus formation, and that continued existence of a stent in a blood vessel can lead to weakening of the blood vessel wall, possibly leading to arterial rupture or the formation of aneurisms. The stent can also become covered by endothelial tissue after implantation of the stent, after which the usefulness of the stent may be substantially diminished, and the continued presence of the stent may cause a variety of problems or complications.

It is therefore desirable that the material of the stent be biodegradable, or bioabsorbable, to reduce the risk of thrombosis or injury to the blood vessel. It is also desirable that the stent be formed of material of minimal thickness, so as to minimize blood flow blockage and facilitate biodegradability and bioabsorption. However, the material must have sufficient radial strength to function as a stent, so that it is desirable to reinforce the material, preferably also with biodegradable, bioabsorbable material.

It is also often useful to provide localized pharmacological treatment of a blood vessel at the location being treated with the stent. It would therefore be desirable to form a stent of materials that are capable of absorbing therapeutic drugs and releasing them at a predictable rate for an ascertainable period of time in a blood vessel, that are also biodegradable and bioabsorbable, and that can provide sufficient radial strength to maintain patency of a blood vessel.

Biodegradable fibers have been used in forming bone fixation plates. In using such fibers to form a biodegradable stent, the fibers can be formed as a mesh, which typically does not by itself have sufficient strength when fashioned as a stent to maintain patency of a blood vessel, and it is possible for the fibers to move around and separate. Chemically sizing the fibers to strengthen them can degrade the fibers, and solvent lamination of the fibers to strengthen them can leave an undesirable residue of solvent in the fibers. It would be desirable to strengthen the mesh of fibers and to prevent the fibers of the mesh from separating and moving around by laminating the mesh with a film of biodegradable, bioabsorbable material. However, in order to provide sufficient radial strength to the stent, it has been found that the density of fiber weave in the mesh should be closely packed, while such a close packing of fibers can prevent sufficient penetration of the film laminate into the fiber mesh to provide good bonding of a film to the fibers of the mesh, so that lamination of such a high density fibrous

2 mesh is typically difficult to achieve, and inconsistent. It would be desirable to provide a stent made of a mesh of biodegradable fibers that can be closely packed for strength, and yet further reinforced with a biodegradable film lamination. The present invention meets these needs.

SUMMARY OF THE INVENTION

Briefly, and in general terms, the present invention provides for a biodegradable mesh and film laminate stent and method of manufacture which provides for good bonding of a laminating film to a fibrous mesh layer of the stent by incorporating a biodegradable, low temperature melting polymeric adhesive material into a composite biodegradable fiber mesh, before laminating the composite mesh to a thin film of biodegradable material. The thin biodegradable film strengthens the composite mesh of biodegradable material without significantly increasing the thickness of the composite mesh, and the stent of the invention is easily manufacturable from the composite mesh and film laminate of the invention. The stent is both completely degradable and absorbable within the body, and capable of delivering therapeutic drugs locally within a blood vessel. The multi-layered laminated construction of the stent allows for selection of one or more layers of resorbable material for retaining selected drugs and releasing them within the affected blood vessel upon implantation.

The laminated construction of the stent also allows a plurality of different drug containing materials to be combined in a single stent. Depending upon the construction and lamination of the stent, drugs can be released simultaneously or sequentially, on the exterior surface of the stent to a blood vessel wall, and directly into the bloodstream, as desired.

The invention accordingly provides for a biodegradable mesh and film stent that is formed of a composite mesh material formed of a plurality of fibers of a first biodegradable polymer bonded together with a second biodegradable adhesive polymer having a melting point below that of the first biodegradable polymer. The composite mesh is laminated on at least one side with a thin film of a third biodegradable polymer, which can be different from, or the same as the first or second polymers.

The biodegradable mesh and film laminate is preferably formed as a sheet and cut in a shape that can be used as a stent, such as a "belt-buckle" type shape that can be joined in a contractible, expandable loop. The stent is preferably cut in such a shape from the sheet of biodegradable mesh and film laminate to have first and second ends, and a main body portion between the first and second ends. The first end preferably includes a slot for receipt of the second end, so that the second end and main body portion are insertable through the slot so as to form a cylindrical loop. The second end includes means for retaining the second end inserted in the slot, and the main body portion includes means for releasably engaging the slot to adjustably retain the main body portion in the slot, so that the stent can be placed in a blood vessel in a contracted cylindrical loop, urged into an expanded configuration, such as by an inflation balloon, and locked in the expanded configuration by the means for releasably engaging the slot.

In one preferred aspect of the invention, a biodegradable, laminated, fibrous composite mesh material is formed of a plurality of fibers of a first biodegradable polymer bonded together with a plurality of a second biodegradable adhesive polymer fibers having a melting point below that of the first biodegradable polymer. The fibers of the first biodegradable polymer are preferably made of a biodegradable, bioabsorbable, high modulus material, such as polyglycolic acid (PGA), for example, although other high modulus polymeric fibers such as fibers of poly-L-lactic acid (L-PLA), polyorthoesters, polyanhydrides, polyiminocarbonates, and inorganic calcium phosphate may also be suitable. The material selected for the mesh layer of the present invention must be biodegradable and bioabsorbable, while providing the necessary physical support structure for the construction of the stent. Furthermore, a degree of longitudinal flexibility is desirable in order to facilitate the transportation of the stent to the eventual implantation site in a blood vessel. These requirements are met by polymers such as PGA or L-PLA that have been extruded and oriented to obtain maximum tensile strength and optimal flexural properties.

The plurality of fibers of the second biodegradable adhesive polymer are preferably selected to have a melting point below the melting point of the first biodegradable polymer, to provide an adhesive bonding between the fibers of the first biodegradable polymer of the mesh and the outer film layers during lamination. The fibers of the second biodegradable adhesive polymer are preferably made of polycaprolactone (PCL), poly-DL-lactic acid (DL-PLA), or a combination of L-PLA and PCL. The fibers of the second biodegradable polymer can also be made of other suitable polymers, such as polyorthoesters, aliphatic polycarbonates, and polyphosphazenes. In one preferred embodiment, the composite mesh can have a weave density of at least about 50 fibers per inch, and can be woven in a plain weave pattern of pairs of the first fiber and fibers of the second polymer.

The composite mesh is preferably laminated by heat and pressure on at least one side with a thin film of a biodegradable polymer, capable of being degraded and absorbed by the body, reinforcing the mesh layer, retaining sufficient quantities of particular drugs, and releasing such drugs at a predictable rate when the biodegradable mesh and film stent is implanted in a blood vessel. The thin films with which the mesh is laminated are preferably a biodegradable polymer selected from the group consisting of DL-PLA and L-PLA, or a combination thereof. Such polymers are first intermixed with the drug or drugs to be delivered, and then are either extruded or solvent cast. The drug containing layer or layers, and the mesh layer are preferably subsequently laminated to one another by heat fusion lamination, simultaneously melting the second biodegradable polymer in the mesh and bonding the mesh with the film laminate.

The invention also provides for a method of making a biodegradable composite mesh and film stent, for use in blood vessels, formed of biodegradable polymeric fibers strengthened by bonding with a biodegradable adhesive polymer and laminated with a biodegradable polymeric film. In one preferred embodiment, the composite mesh is formed from a weave formed from a plurality of high strength fibers made of a first biodegradable polymer, and a plurality of lower temperature melting fibers made of a second biodegradable polymer. In an alternate embodiment, the high strength fibers are commingled with the lower temperature melting fibers. In another alternate embodiment, a plurality of the high strength biodegradable fibers are coated with the low temperature melting biodegradable polymer, and in a variation of this embodiment, the high strength biodegradable fibers are individually coated with the lower temperature melting biodegradable polymer, and are used to weave the mesh. The composite mesh is covered on at least one side by a laminating film, and is preferably placed between laminating films, and laminated at an elevated temperature, to melt the lower temperature melting biodegradable polymer to produce the biodegradable composite mesh and film. The laminated biodegradable mesh and film material can then be cut, preferably with a laser, to form the stent.

The laminated construction of the stent allows the mesh layer to be fabricated prior to lamination, and the drug impregnated film layers to be laminated to the mesh after fabrication of the mesh is complete, thereby avoiding deterioration or degradation of the drugs that might otherwise occur during the fabrication of the mesh.

These and other aspects and advantages of the invention will become apparent from the following detailed description, and the accompanying drawings, which illustrate by way of example the features of the invention.

DETAILED DESCRIPTION OF THE PREFERRED EMBODIMENTS

Figure 1:
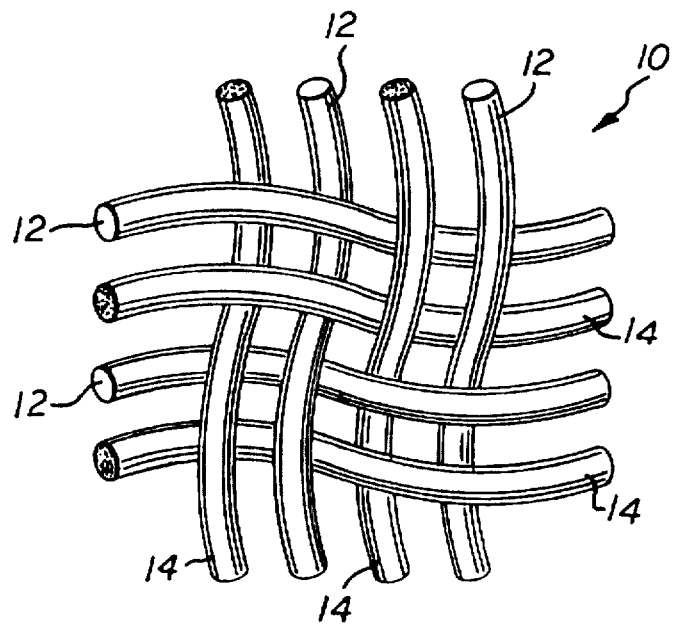
FIG. 1 is an enlarged top plan view of a small section of a biodegradable mesh weave of high strength and low temperature melting fibers according to the principles of the invention.

Continued exposure of a stent to blood can lead to undesirable thrombus formation, and continued existence of a stent in a blood vessel can lead to a variety of problems or complications. However, forming the stent to be of minimal thickness to facilitate biodegradability and bioabsorption also weakens the radial strength necessary for the stent to maintain blood vessel patency. A mesh of biodegradable fibers can form a thin material for making a stent, and can be strengthened and prevent separation and movement of the fibers in the mesh by laminating the mesh with a film of biodegradable, bioabsorbable material. However, closely packing the fibers of the mesh to provide sufficient radial strength to the stent can interfere with adequate bonding of the film layers to the mesh.

The invention is accordingly embodied in a biodegradable mesh and film stent and a method of manufacturing the stent which involves incorporating a biodegradable, low temperature melting adhesive material into the biodegradable fiber mesh, and laminating the composite mesh on at least one side with a thin reinforcing film of biodegradable material.

As is illustrated in the drawings, in one preferred embodiment, a biodegradable laminated fibrous mesh 10 is formed from a weave of a plurality of fibers of a high strength biodegradable polymer 12 and a plurality of fibers of a second biodegradable polymer 14 that melts at a lower temperature than the first biodegradable polymer will melt. As used in this description, the terms biodegradable, bioabsorbable, resorbable, degradable, and absorbable are meant to encompass materials that are broken down and gradually absorbed or eliminated by the body, whether these processes are due to hydrolysis or metabolic processes.

The mesh layer comprises the main structural component of the stent, and provides the principal necessary physical characteristics for the stent. This enables the stent to maintain the patency of the blood vessel in which it is implanted, and provides the desired flexural characteristics to the stent to allow it to be moved into position and expanded. The fibers can readily be woven together in accordance with principles known to a person skilled in the art, with reference to this description. The high strength fibers are preferably made of a first biodegradable, bioabsorbable, high modulus polymer, such as polyglycolic acid (PGA), for example, although other high modulus polymeric fibers such as fibers of poly-L-lactic acid (L-PLA), polyorthoesters, polyanhydrides, polyiminocarbonates, and or biodegradable inorganic fibers, such as the family of calcium phosphates, may also be suitable. Other biodegradable, bioabsorbable polymers, such as polyorthoesters and polyanhydrides may also be suitable. In this preferred embodiment, the second fiber woven in the mesh is preferably a second biodegradable polymer fiber having a melting point below that of the first biodegradable polymer. The second, relatively lower temperature melting biodegradable polymer can be, for example, polycaprolactone (PCL), poly-DL-lactic acid (DL-PLA), or a combination of L-PLA and PCL, to provide an adhesive bonding between the first polymeric fibers of the mesh and the outer film layers during lamination. The second plurality of biodegradable adhesive polymer fibers can also be made of other suitable polymers, such as polyorthoesters, aliphatic polycarbonates, and polyphosphazenes. In one aspect of the invention the melting point of the second biodegradable polymer can be up to about 200° C. (about 392° F.), although the melting point of the second biodegradable polymer can vary, depending upon the specific polymer or polymers selected as the relatively higher melting first biodegradable polymer and as the relatively lower temperature melting second biodegradable polymer. The fibers are typically about 0.0001 in. to about 0.002 in. in diameter. PGA fibers are typically about 5–7 gm/denier, while DL-PLA fibers are typically about 2–3 gm/denier.

Figure 2:
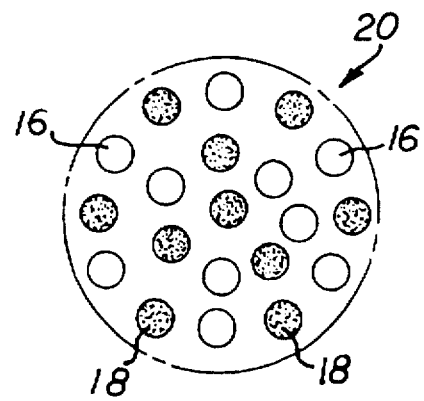
FIG. 2 is an enlarged cross-sectional view of an alternate composite fiber for making the biodegradable mesh, formed of commingled high strength and low temperature melting fibers.
Figure 3:
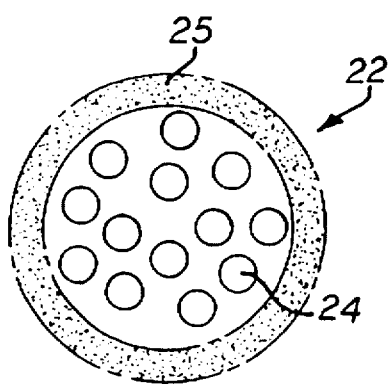
FIG. 3 is an enlarged cross-sectional view of a second alternate composite fiber for making the biodegradable mesh, formed by coating the high strength fibers with a low temperature melting polymer.
Figure 4:
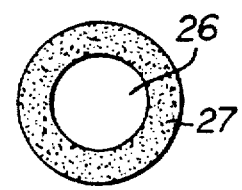
FIG. 4 is an enlarged cross-sectional view of a third alternate composite fiber to be used in weaving the biodegradable mesh, formed by coating individual high strength fibers with a low temperature melting polymer.

In one preferred weave, as shown in FIG. 1, the composite mesh formed by the two fibers is woven in a two-over-two plain weave pattern of pairs of the high strength and lower melting fibers, and preferably has a weave density of at least about 50 fibers per inch. However, the weave density can vary considerably, such as from approximately 10 fibers per inch to approximately 200 fibers per inch, for example, depending upon the thickness of materials selected. Coweaving the high strength fibers and low temperature melting fibers in this manner intimately mixes the fibers, eliminating the need for high pressures and temperatures to achieve good bonding during lamination, and the composite mesh 10 of fibers can be produced in this manner with simple weaving equipment well known to those skilled in the art. The ratio of high strength fibers to the lower melting polymer fibers can be optimized with other fiber ratios as well, such as three high melt fiber plus one low melt fiber, one high melt fiber plus three low melt fibers, two high melt fibers plus one low melt fiber, or one high melt fiber plus two low melt fibers, for example, and in different weave patterns such as three-over-one, one-over-three, two-over-one, or one-over-two weaves, and the like, to provide the desired strength and close packing of the biodegradable fibrous mesh preparatory to lamination. The mesh is typically about 0.0002 in. to about 0.005 in. thick, or can be thicker for larger stents, such as for peripheral arteries, for example. When heated during lamination, the low temperature melting fibers serve as an adhesive, strengthening the mesh, due to the bonding of the higher melting, high strength fibers and the lower melting fibers together under heat and pressure. Alternatively, the higher temperature melting, high strength fibers 16 can be commingled with the lower temperature melting fibers 18 to make a composite fiber 20 for forming, the composite mesh, as is illustrated in FIG. 2. In another alternative embodiment, a similar composite fiber 22 can be formed for making the mesh by coating a plurality of the higher temperature melting, high strength fibers 24 with the lower temperature melting polymer 25, as is illustrated in FIG. 3. In a variation of this embodiment, individual higher temperature melting, high strength fibers 26 can be coated with the lower temperature melting polymer 27, to be used in weaving the biodegradable mesh, as is shown in FIG. 4.

Figure 6:
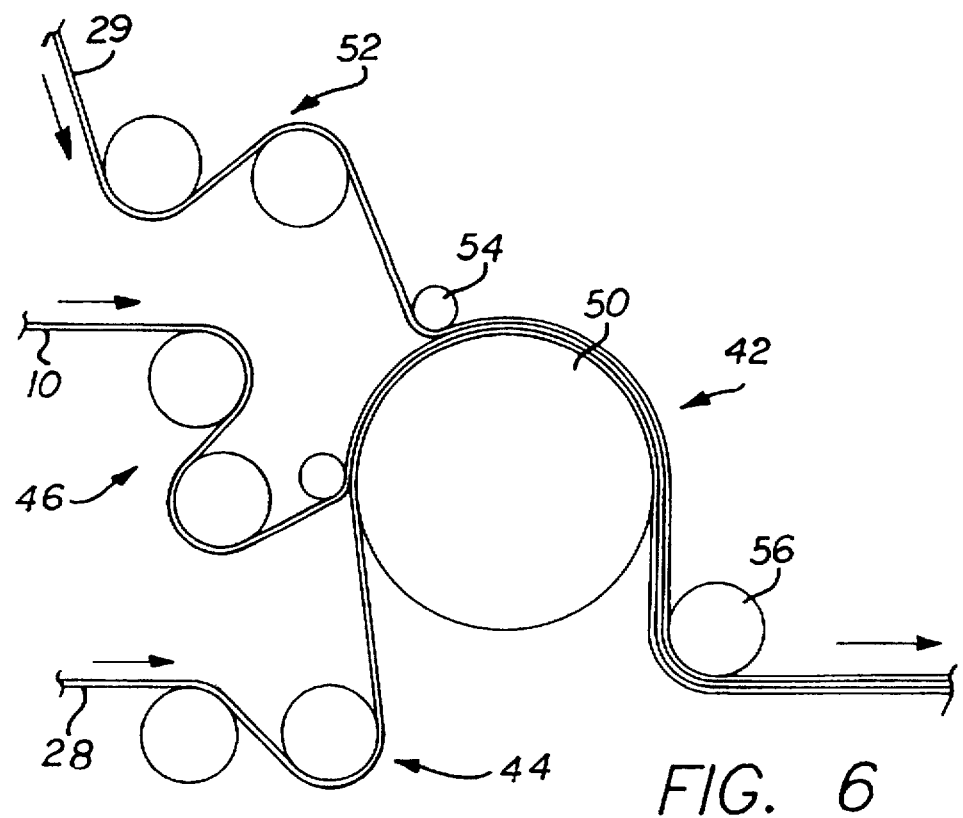
FIG. 6 is a diagrammatic view of a lamination apparatus that can be used for laminating the mesh on two sides with a biodegradable film.
Figure 7:
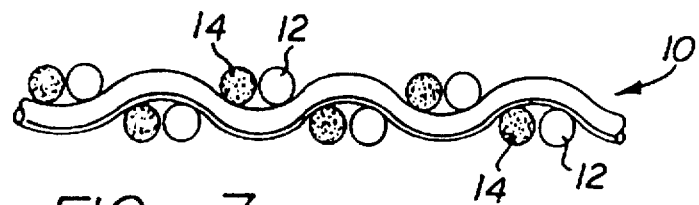
FIG. 7 is an enlarged cross-sectional view of a biodegradable mesh according to the principles of the invention.
Figure 8:
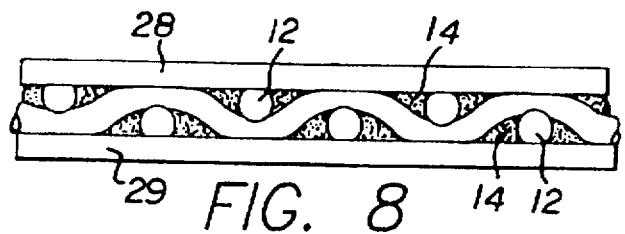
FIG. 8 is an enlarged cross-sectional view of the biodegradable mesh and film laminate following melting of the lower melting biodegradable polymer fibers of the mesh during lamination.

The composite mesh 10 of the biodegradable high strength fibers 12 and lower melting biodegradable polymer 14 is preferably laminated with a biodegradable polymeric film 28,29 such as DL-PLA or L-PLA. The polymeric film is typically about 0.0005 in. to about 0.005 in. thick, or can be thicker for peripheral artery applications. When laminated on two sides, the laminated mesh can be approximately 0.001 in. to 0.025 in. thick; and when laminated on only one side, the laminated mesh can be approximately 0.0007 in. to 0.020 in. thick, for example. The layers of biodegradable polymeric film 28 on either side of the mesh 10 are selected for their ability to reinforce the mesh, and to absorb and release drugs at predictable rates when the stent is implanted in a blood vessel or other lumen in the body. As is illustrated in FIG. 6, the biodegradable polymeric film layers 28, 29 are disposed so that each layer of film applied contacts the surface of the mesh. The biodegradable polymeric film layers can contain the same or different drugs, or combinations of drugs. Alternatively, only one drug releasing layer may be applied to the surface of the mesh, or additional layers of biodegradable polymeric film can be built up on top of one another for sequential release of drugs absorbed within them.

The dimensions of the stent as well as its ultimate strength and physical characteristics, in addition to the particular drugs and drug delivery rates are selected for the particular application of the stent. For example, it would desirable for stents according to the principles of the invention to be implanted in coronary arteries to release drugs that can control thrombosis from the inner layer of the stent which is exposed to the bloodstream. Appropriate drugs for this purpose include heparin and prostacyclin, and the like. The film layer to be used as the outer layer of the stent can also be provided with drugs such as angiopeptin, methotrexate, and heparin, to control restenosis.

Figure 5:
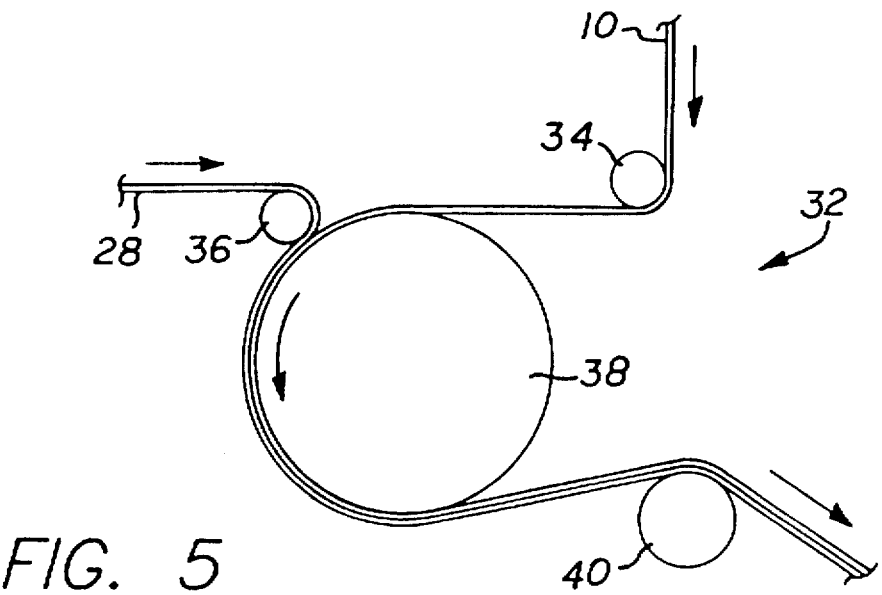
FIG. 5 is a diagrammatic view of a laminating apparatus that can be used for laminating the mesh on one side with a biodegradable film.

The mesh is formed as a sheet, and is typically first cut into squares or strips of a suitable size for the lamination equipment. When the mesh is to be laminated on one side only, the mesh and film laminate can be bonded by a typical two-ply fusion lamination system 32, as is illustrated in FIG. 5. The two ply laminating stack typically includes an idler roll 34 receiving the mesh 10, and a lay on roll 36 receiving the laminating film 28. The mesh 10 and laminating film 28 are pressed into intimate contact between the lay on roll and the heating and combining drum 38, and can be heated by the drum and take off heat roll 40, where the biodegradable mesh and film laminate can be utilized for further processing in making the mesh and film stent.

When the mesh is to be laminated on both sides, the mesh 10 and film layers 28, 29 can be bonded together by typical three-ply fusion lamination rolls, as is illustrated in FIG. 6. Such a three-ply fusion lamination system 42 can typically include a first preheat roll system 44 for receiving and-preheating one laminating film 28, a second preheat roll system 46 for receiving and preheating the mesh 10, and a lay on roll 48 for pressing the fibrous mesh and first laminating film together in intimate contact against the heating and combining drum 50. A third preheat roll system 52 can be provided receiving and preheating the second laminating film 29, and a lay on roll 54 presses the second laminating film and mesh together in intimate contact against the drum. The mesh and two layers of laminating film can be further heated by the drum and take off heat roll 56, and removed for further processing in making the mesh and film stent. Other laminating systems that combine the mesh with one or more of the laminating films and heat the mesh to melt the low temperature melting polymer during the lamination process to produce the film with a reinforced polymer weave may also be suitable. In one implementation of the invention, the mesh and laminating films are typically heated during lamination to a temperature in the range of from about 120° to about 330° F. (about 48.9° to 165.6° C.), and most preferably from about 180° to 270° F. (about 82.2° to 132.2° C.), to melt the low temperature melting polymer fiber to produce the biodegradable composite mesh and film. In testing with a three-roll stack type of fusion lamination equipment, it was found that adequate bonding of the film layer to the mesh typically occurred when the lamination was performed at a roll speed of about 0.2–5 feet per minute, and preferably at about 1.5 feet per minute, with a silicone release film. The ranges of laminating temperatures and appropriate roll speeds for the lamination equipment can be expected to vary for different types of equipment, and with different thicknesses and types of materials. For improved adhesion of the thin film to the mesh, the mesh can optionally be dipped in a suitable adhesive before laminating the thin film to the mesh. After the lamination process is complete, the biodegradable mesh and film material can then be cut, preferably with a laser, such as a continuous $CO_2$ laser, a pulsed YAG laser, or an excimer laser, for example, or alternatively, by stamping, to form the stent.

Figure 9:
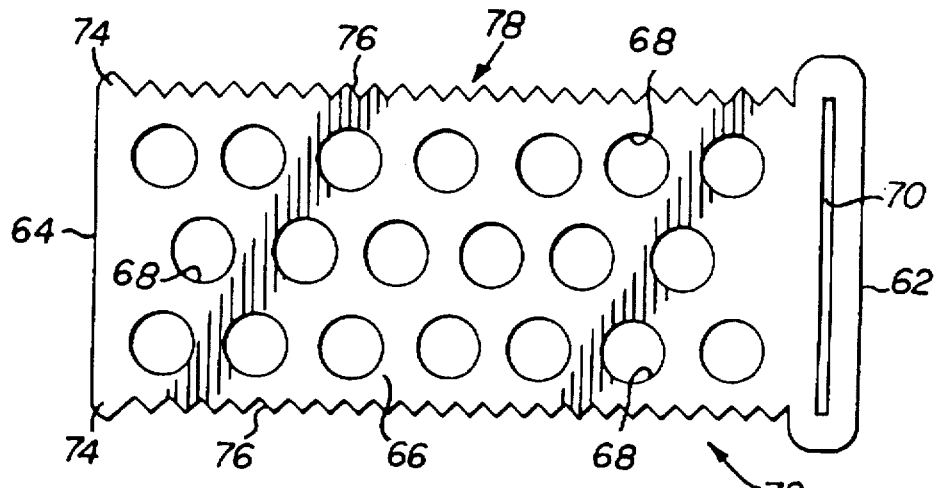
FIG. 9 is a top plan view of a biodegradable mesh and film stent according to the principles of the invention.
Figure 10:
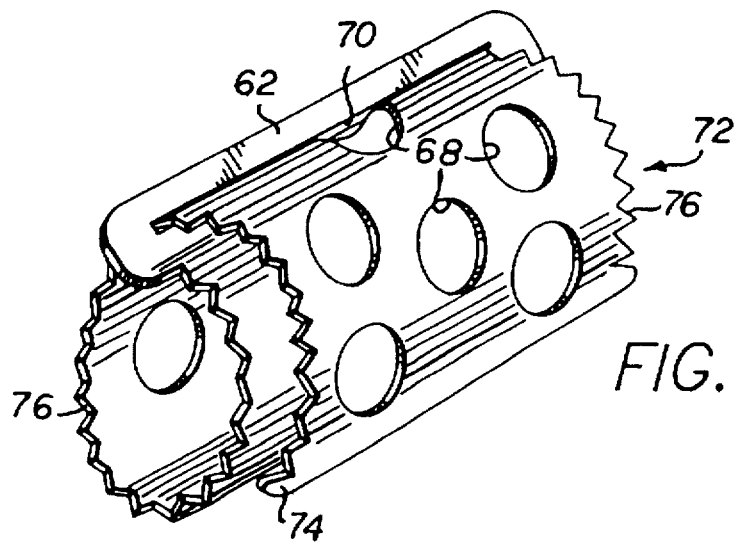
FIG. 10 is a perspective view of the biodegradable mesh and film stent of FIG. 9 joined in a loop configuration.

The biodegradable mesh and film laminate is preferably cut in a shape that can be used as a stent 60, such as the "belt-buckle" shape illustrated in FIG. 9, so that the ends of the stent can be joined to form a contractible, expandable loop, as shown in FIG. 10. The stent 60 preferably includes a first end 62, a second end 64, and a main body portion 66 between the first and second ends. The main body portion can also include a plurality of apertures 68 to facilitate the process of degradation and absorption of the stent once it is implanted. The first end preferably includes a slot 70 for receiving and retaining the second end. The second end and main body portion are thus insertable through the slot so as to form a cylindrically, loop shaped stent 72 that can be furled and contracted for placement within a blood vessel. The second end includes a widened portion 74 for retaining the second end inserted in the slot, and the main body portion includes a plurality of serrations 76 along each side 78 of the main body portion dimensioned to provide a firm interference fit in the slot, for releasably engaging the slot to adjustably retain the main body portion in the slot. The stent can be placed in a blood vessel in a furled, cylindrical, contracted loop configuration with a sufficiently small outer diameter so as to be transportable through the targeted blood vessel or other lumen, and of a sufficiently large internal diameter to receive an inflation balloon device (not shown) therein. The stent can thus be urged into an unfurled, expanded configuration by inflation of the inflation balloon device, and locked in the desired expanded configuration by the serrations on the sides of the main body portion so that the stent cannot recontract.

It has thus been demonstrated that the invention provides for a stent made of a mesh of biodegradable fibers that can be closely packed for strength, and that is further reinforced with a biodegradable film lamination. The method of manufacture of the biodegradable mesh and film stent of the invention provides for good bonding of the laminating film to the fibrous mesh layer of the stent by incorporating a relatively lower temperature melting, biodegradable polymeric material into a composite biodegradable fiber mesh. The composite mesh is then laminated with a thin film of biodegradable material that strengthens the composite mesh of biodegradable material without significantly increasing the thickness of the composite mesh. Lamination of the mesh of the stent with one or more film reinforcing layers that can absorb and release drugs allows selected drugs to be released within the affected blood vessel upon implantation.

In the foregoing description, statements concerning specific dimensions, temperatures, weave patterns and weave densities are given by way of example, and it should be apparent to one of ordinary skill in the art that other similar dimensions, temperatures, weave patterns and weave densities may also be suitable according to the principles of the invention. It should also be readily apparent that a stent according to the principles of the invention can also be utilized to treat other conditions of vessels or lumens within the body, such as abdominal aorta aneurism, or prostate cancer, for example, in which a stent can be placed within the urethra, and a chemotherapeutic drug can be released directly into the urethra.

It will therefore be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A biodegradable mesh and film stent for use in maintaining the patency of blood vessels, said stent comprising:

a mesh layer having first and second sides, formed from a plurality of fibers of a first biodegradable polymer, said plurality of fibers being heat bonded together with a second biodegradable polymer;

at least one layer of a film of a biodegradable polymer bonded to said mesh layer on at least one side of said mesh layer to form a sheet of biodegradable mesh and film material;

said sheet of biodegradable mesh and film material having first and second ends and a main body portion between said first and second ends, said sheet of biodegradable mesh and film material being rolled up into a cylindrical configuration whereby said first end overlaps said second end.

2. The stent of claim 1, wherein said first biodegradable polymer is selected from the group consisting of polyglycolic acid, poly-L-lactic acid, polyorthoesters, polyanhydrides, polyiminocarbonates, and inorganic calcium phosphate.

3. The stent of claim 1, wherein said second biodegradable polymer is selected from the group consisting of polycaprolactone, poly-DL-lactic acid, a combination of poly-L-lactic acid and polycaprolactone, polyorthoesters, aliphatic polycarbonates, polyphosphazenes, and combinations thereof.

4. The stent of claim 1, wherein said mesh layer of fibers of a first biodegradable polymer has a weave density of from about 10 to about 200 fibers per inch.

5. The stent of claim 1, wherein said mesh layer is laminated with a layer of film on both sides to encapsulate the mesh.

6. The stent of claim 1, wherein said laminating layer of film is formed from a biodegradable polymer selected from the group consisting of poly-DL-lactic acid and poly-L-lactic acid.

7. A biodegradable mesh and film stent for use in maintaining the patency of blood vessels, said stent comprising:
 a mesh layer having first and second sides, formed from a plurality of fibers of a first biodegradable polymer, said plurality of fibers being heat bonded together with a second biodegradable polymer;
 at least one layer of a film of a biodegradable polymer bonded to said mesh layer on at least one side of said mesh layer to form a sheet of biodegradable mesh and film material;
 said sheet of biodegradable mesh and film material having first and second ends and a main body portion between said first and second ends, said first end having a surface defining a slot for receiving said second end, said second end and said main body portion being insertable through said slot so as to form a loop, said second end having means for retaining said second end inserted in said slot, and said main body portion having means for releasably engaging said slot to adjustably retain said main body portion in said slot.

8. The stent of claim 7, wherein said first biodegradable polymer is selected from the group consisting of polyglycolic acid, poly-L-lactic acid, polyorthoesters, polyanhydrides, polyiminocarbonates, and inorganic calcium phosphate.

9. The stent of claim 7, wherein said second biodegradable polymer is selected from the group consisting of polycaprolactone, poly-DL-lactic acid, a combination of poly-L-lactic acid and polycaprolactone, polyorthoesters, aliphatic polycarbonates, polyphosphazenes, and combinations thereof.

10. The stent of claim 7, wherein said mesh layer of fibers of a first biodegradable polymer has a weave density of from about 10 to about 200 fibers per inch.

11. The stent of claim 7 wherein said mesh layer is laminated with a layer of film on both sides to encapsulate the mesh.

12. The stent of claim 7 wherein said laminating layer of film is formed from a biodegradable polymer selected from the group consisting of poly-DL-lactic acid and poly-L-lactic acid.

13. The stent of claim 7 wherein said means for retaining said second end inserted in said slot comprises a widened portion of said second end.

14. The stent of claim 7, wherein said main body portion includes first and second side edges, and said means in said main body portion for releasably engaging said slot to adjustably retain said main body portion in said slot comprises a plurality of serrations along each side edge of the main body portion dimensioned to provide a firm interference fit in the slot.

15. A method of making a biodegradable mesh and film stent for use in maintaining the patency of blood vessels, comprising the steps of:
 forming a sheet of biodegradable mesh and film material from a plurality of fibers of a first biodegradable polymer and a second biodegradable polymer, said second biodegradable polymer melting at a lower temperature than the first biodegradable polymer;
 placing at least one laminating film of a biodegradable polymer, on at least one side of said mesh;
 heating said laminating film and mesh to melt said second biodegradable polymer and form a mesh and film laminate; and
 cutting the sheet of biodegradable mesh and film material in a shape to form said stent, said stent being formed to include first and second ends and a main body portion between said first and second ends; and
 rolling said sheet of biodegradable mesh and film material into a cylindrical configuration whereby said first end overlaps said second end.

16. The method of claim 15, wherein said mesh and film are heated to a temperature of from about 120° to about 330° F.

17. The method of claim 15, wherein said mesh and film are heated to a temperature of from about 180° to about 270° F.

18. The method of claim 15, wherein said step of forming a mesh comprises coweaving a fiber of said first biodegradable polymer with a fiber of said second relatively lower temperature melting biodegradable polymer.

19. The method of claim 18, wherein said step of forming a mesh comprises coweaving a plurality of said fibers of said first biodegradable polymer and a plurality of fibers of said second relatively lower temperature melting biodegradable polymer.

20. The method of claim 19 wherein said step of coweaving comprises coweaving pairs of said first biodegradable polymeric fiber and said fibers of said second low temperature melting biodegradable polymer in a plain weave pattern.

21. The method of claim 15, wherein said step of forming a mesh comprises commingling said plurality of said first biodegradable polymeric fibers and a plurality of fibers of said second low temperature, melting biodegradable polymer to form a plurality of commingled fibers of said first and second polymers, and weaving said commingled fibers in a mesh.

22. The method of claim 15, wherein said step of forming a mesh comprises coating said plurality of fibers of said first biodegradable polymer with said second low temperature melting biodegradable polymer, and weaving a mesh of said plurality of said first biodegradable polymeric fibers coated with said second low temperature melting biodegradable polymer.

23. The method of claim 15, wherein said step of forming a mesh comprises coating a plurality of individual fibers of said first biodegradable polymer with said second lower temperature melting biodegradable polymer to form a plurality of individually coated fibers of said first biodegradable polymer, and weaving a mesh of said plurality of individually coated fibers of said first biodegradable polymer.

24. The method of claim 15, wherein said step of cutting said sheet of biodegradable mesh and film material comprises cutting said mesh and film laminate with a laser.

25. A method of making a biodegradable mesh and film stent for use in maintaining the patency of blood vessels, comprising the steps of:

forming a mesh of a plurality of fibers of a first biodegradable polymer and a second biodegradable polymer, said second biodegradable polymer melting at a lower temperature than the first biodegradable polymer;

placing at least one laminating film of a biodegradable on at least one side of said mesh;

heating said laminating film and mesh to melt said second biodegradable polymer and form a mesh and film laminate; and cutting the mesh and film laminate in a shape to form said stent, said stent being formed to include first and second ends and a main body portion between said first and second ends, said first end having a surface defining a slot for receiving said second end, said second end and said main body portion being formed to be insertable through said slot so as to form a loop, said second end being formed to include means for retaining said second end inserted in said slot, and said main body portion being formed to have means for releasably engaging said slot to adjustably retain said main body portion in said slot.

26. The method of claim 25, wherein said laminating film and mesh are heated to a temperature of from about 120° to about 330° F.

27. The method of claim 25, wherein said step of laminating said mesh is carried out at a temperature of from about 180° to about 270° F.

28. The method of claim 25, wherein said step of forming a mesh comprises coweaving a fiber of said first biodegradable polymer with a fiber of said second relatively lower temperature melting biodegradable polymer.

29. The method of claim 28, wherein said step of forming a mesh comprises coweaving a plurality of said fibers of said first biodegradable polymer and a plurality of fibers of said second relatively lower temperature melting biodegradable polymer.

30. The method of claim 29, wherein said step of coweaving comprises coweaving pairs of said first biodegradable polymeric fiber and said fibers of said second low temperature melting biodegradable polymer in a plain weave pattern.

31. The method of claim 25, wherein said step of forming a mesh comprises commingling said plurality of said first biodegradable polymeric fibers and a plurality of fibers of said second low temperature melting biodegradable polymer to form a plurality of commingled fibers of said first and second polymers, and weaving said commingled fibers in a mesh.

32. The method of claim 25, wherein said step of forming a mesh comprises coating said plurality of fibers of said first biodegradable polymer with said second low temperature melting biodegradable polymer, and weaving a mesh of said plurality of said first biodegradable polymeric fibers coated with said second low temperature melting biodegradable polymer.

33. The method of claim 25, wherein said step of forming a mesh comprises coating a plurality of individual fibers of said first biodegradable polymer with said second lower temperature melting biodegradable polymer to form a plurality of individually coated fibers of said first biodegradable polymer, and weaving a mesh of said plurality of individually coated fibers of said first biodegradable polymer.

34. The method of claim 25 wherein said step of cutting said mesh and film laminate comprises cutting said mesh and film laminate with a laser.

* * * * *

UNITED STATES PATENT AND TRADEMARK OFFICE
CERTIFICATE OF CORRECTION

PATENT NO. : 5,766,710
DATED : Jun. 16, 1998
INVENTOR(S) : Todd Hanson Turnlund, Robert Paul Eury It is certified that error appears in the above-identified patent and that said Letters Patent is hereby corrected as shown below:

Column 11, Claim 25, Line 13, After "biodegradable", add --polymer--.

Signed and Sealed this

Eighth Day of September, 1998

Attest:

BRUCE LEHMAN

Attesting Officer      Commissioner of Patents and Trademarks